United States Patent [19]

Ito

[11] Patent Number: 4,896,961
[45] Date of Patent: Jan. 30, 1990

[54] PARTICLE ANALYZING APPARATUS

[75] Inventor: Yuji Ito, Chigasaki, Japan

[73] Assignee: Canon Kabushiki Kaisha, Tokyo, Japan

[21] Appl. No.: 368,151

[22] Filed: Jun. 15, 1989

Related U.S. Application Data

[63] Continuation of Ser. No. 106,025, Oct. 8, 1987, abandoned, which is a continuation of Ser. No. 811,462, Dec. 20, 1985, abandoned.

[30] Foreign Application Priority Data

Dec. 26, 1984 [JP] Japan ................................ 59-278154

[51] Int. Cl.$^4$ ....................... G01N 21/64; G01N 21/53
[52] U.S. Cl. ................................ 356/73; 250/461.2; 356/339; 356/417
[58] Field of Search ................ 356/73, 336, 338, 339, 356/318, 417; 250/461.2

[56] References Cited

U.S. PATENT DOCUMENTS

| | | | |
|---|---|---|---|
| 2,775,159 | 12/1956 | Frommer | 356/339 |
| 3,504,183 | 3/1970 | Salkowski | 356/338 |
| 3,824,402 | 7/1974 | Mullaney et al. | 356/73 |

Primary Examiner—Richard A. Rosenberger
Attorney, Agent, or Firm—Fitzpatrick, Cella, Harper & Scinto

[57] ABSTRACT

A particle analyzing apparatus has an irradiating optical system for irradiating a particle to be examined with a light beam, a measuring optical system for measuring the light scattered by the particle, a device provided in the irradiating optical system for varying the form of the light beam, and a device provided at a position in the measuring optical system optically conjugate with the position of the particle to be irradiated with the light beam and adapted for varying the form of viewing field when the form of the light beam is varied.

9 Claims, 2 Drawing Sheets

PARTICLE ANALYZING APPARATUS

This application is a continuation of application Ser. No. 106,025 filed Oct. 8, 1987, which is a continuation of application Ser. No. 811,462, filed Dec. 20, 1985, both now abandoned.

BACKGROUND OF THE INVENTION

1. Field of the Invention

The present invention relates to a particle analyzing apparatus, and in particular to a flow cytometer in which a laser light is applied to a hydrodynamically converged portion of a cell-suspended solution flowing at a high speed, wherein the forward scattered light and laterally scattered light or scattered fluorescent light are detected in the sucession to analyze the properties and structure of the cellular particle.

2. Description of the Prior Art

As shown in FIGS. 1 and 2 of the accompanying drawings, in a flow cytometer, a cell-suspended solution flows to a flow section 2 of a minute rectangular cross section (e.g. 70 $\mu m \times 20$ $\mu m$) in a flow cell 1 together with sheath liquid around said solution, and is hydrodynamically converged. An irradiating light is also converged at the same position, and forward scattered light is detected by a photodetector 8 through a lens 7, while laterally scattered light or fluorescent light is detected by a photodetector 15 through a lens 9.

The form of the irradiating beam in the flow cell is varied according to the size of the particle to be examined or the purpose of analysis. For example, if emphasis is to the examination of morphology of a cell, there is employed a laser beam of a slit form of about 4 $\mu m$ wide, in order to identify the maximum diameter of the cell and nucleus, ratio of diameter of nucleus to cell, position of nucleus, and whether the cell is a polykaryocyte. On the other hand, the prior art has not generally give particular consideration to the form of the viewing field in the light measuring unit, and the accuracy of analysis cannot be improved due to a possibility of receiving pseudo signals from objects other than the particle to be examined.

More specifically, in FIG. 2, a change in the form of the irradiating beam causes changes in the sizes of the beam in the y- and z-directions in the flow section 2. For example, in case the form of the irradiating beam is so changed as to reduce the size of the beam in the y- and z-directions, the size of the viewing field receiving the light in the z-direction is reduced in the optical system for measuring the laterally scattered light, and same also applies in the x-direction if the particle size is small. Thus, pseudo signals from objects other than the particle to be examined are unavoidable if the form of the viewing field of the measuring optical system is not changed.

SUMMARY OF THE INVENTION

An object of the present invention is to provide a particle analyzing apparatus in which the accuracy of measurement is not affected by a change in the form of the irradiating beam in the flow cell.

Another object of the present invention is to provide a particle analyzing apparatus in which the accuracy of measurement is automatically maintained at a determined level when the form of the irradiating beam is changed.

DESCRIPTION OF THE PREFERRED EMBODIMENTS

Figure 1:
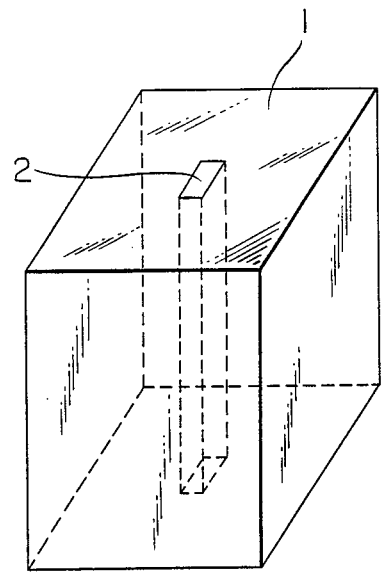
FIG. 1 is a schematic view of a flow cell.
Figure 2:
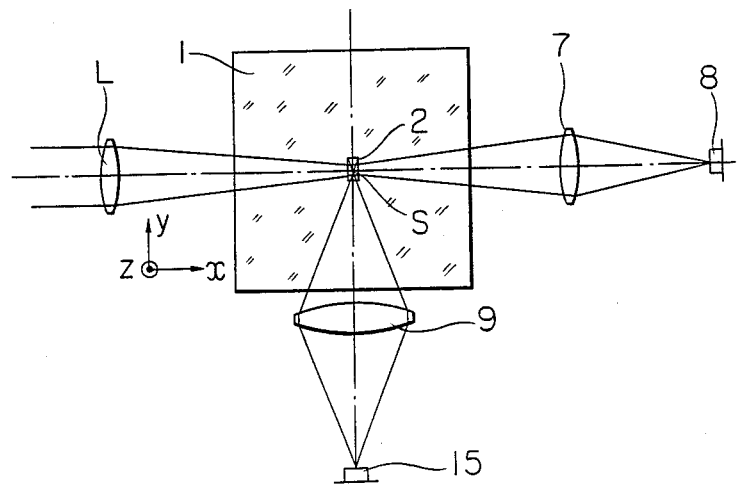
FIG. 2 is a schematic view of a conventional structure.
Figure 3:
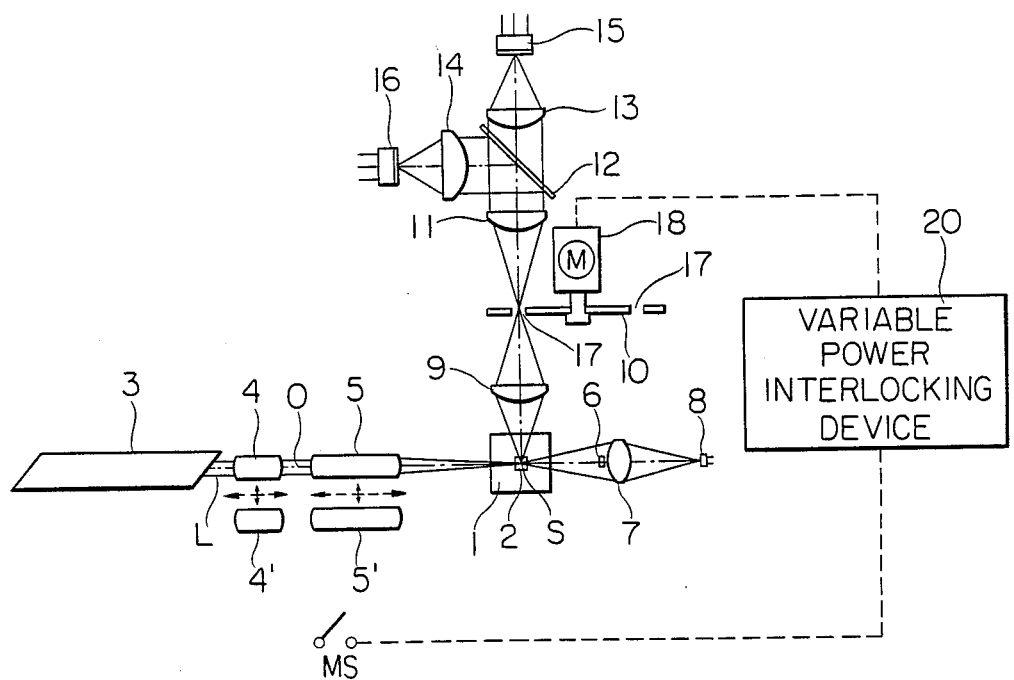
FIG. 3 is a view showing an embodiment of the present invention.

FIG. 3 shows a particle analyzing apparatus embodying the present invention, wherein a laser unit 3 is provided perpendicularly to z-axis at the center of a flow S of particles to be examined, which passes, perpendicularly to the plane of drawing, through a flow section 2 at the center of a flow cell 1. On the optical axis O of a laser light L emitted by the laser unit 3, and at the side of said laser unit 3 with respect to the particle S to be examined, there are provided beam diameter varying means 4, consisting of a beam expander or a beam compressor, and a cylindrical lens system for converging the beam to a particle S to be present at the center of the flow section 2. The beam diameter varying means 4 is rendered interchangeable with another beam diameter varying means 4', while the cylindrical lens system 5 is rendered interchangeable with another cylindrical lens system 5'. The beam diameter varying means 4 and the cylindrical lens system 5 may be replaced by a "Zoom"-type lens movable in the axial direction. Also on the optical axis O and opposite to the laser unit 3 with respect to the flow cell 1, there are provided in succession a light shield plate 6, a condenser lens 7 and a photoelectric detector 8.

In a direction substantially perpendicular to the optical axis O of the laser light L and to the axis Z of the flow of the particle S to be examined, there are provided in succession a condenser lens 9, a diaphragm plate 10, a lens 11 and a beam splitter 12 (generally a half mirror or a dichroic mirror) and condenser lenses 13, 14 and photoelectric detectors 15, 16 are provided respectively on two optical axes split by said beam splitter positioned diagonally to the optical axis of the lenses 9, 11. The diaphragm plate 10 is drive by a motor 18 in such a manner that diaphragms 17 on said diaphragm plate 10 are placed optically conjugate with the flow section 2 with respect to the condenser lens 10.

Figure 4:
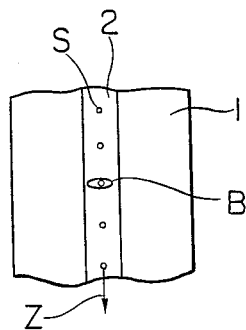
FIG. 4 is a cross-sectional view of a flow cell.

Thus, the laser light L emitted by the laser unit 3 is shaped into a circle of a suitable diameter by the beam diameter varying means 4, and falls, in an oval form, onto the flow section 2 of the flow cell 1 through the cylindrical lens system 5. FIG. 4 shows the relationship between the form of the irradiating beam B and the particle S to be examined.

The minor axis of the oval is in the direction of flow and the major axis is in a perpendicular direction, since the size of beam in the direction of flow is preferably substantially equal to the size of a particle. However, in the perpendicular direction, a larger beam size is selected in order to enable measurement even when the particle shows certain drift.

In case the particle S to be examined is irradiated with a beam of another form, there is another set of beam diameter varying means 4' and cylindrical lens system 5' of a different focal length to provide that the converging position of the beam always coincides with the center of the flow section 2.

The form of said irradiating beam is determined according to the size of the particle S to be examined and to the purpose of analysis.

Among the light irradiating and scattered by the particle S to be examined, the light scattered in the forward direction is focused by the condenser lens 7 onto the photodetector 8 to provide information regarding the size of said particle S. The light transmitted without meeting particle S is eliminated by the shield plate 6.

The laterally scattered light and fluorescent light pass a selected diaphragm 17, and are then transformed into a parallel beam by the lens 11 and divided by the beam splitter 12 into laterally scattered and fluorescent light, which are respectively detected by the photodetectors 15, 16 through the condenser lenses 13, 14. The laterally scattered light serves as an indication of granularity inside the particle to be examined, while the fluorescent light serves to identify biochemical properties of said particle.

In the present embodiment, selection of diaphragms 17 is executed for determining the view field form as follows. A variable power (magnification interlocking) device 20 detects an interchange from the optical systems 4, 5 to another optical systems 4', 5' in the irradiating laser light L for example through a microswitch MS to activate the motor 18, thus rotating the diaphragm plate 10 to bring a predetermined diaphragm 17 to a position optically conjugate with the particle S positioned at the center of the flow section 2 with respect to the imaging lens 9. In this manner the diaphragm 17 of a determined form is easily selected in response to a change in the form of the irradiating beam B in the flow cell 1.

Figure 5:
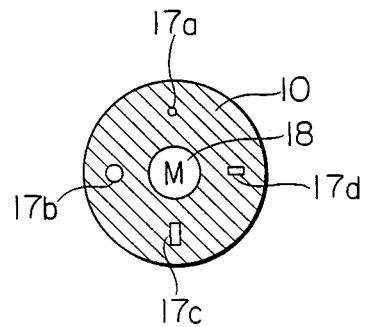
FIG. 5 is a plan view of a diaphragm plate.

FIG. 5 shows a specific example of the diaphragm plate 10 to be driven by the motor 18. The plate 10 is provided with diaphragms 17a, 17b, 17c, 17d of different forms so that a diaphragm of a form approximately resembling the form of the laser beam B irradiating the particle S may be selected. For example, when the irradiating beam is oval, there is selected a diaphragm 17c or 17d of a rectangular shape which is circumscribed about said oval, and when the irradiating beam is circular wherein employed is a beam form varying optical system not involving the cylindrical lens system 5), there is selected a circular diaphragm 17a or 17b.

Although there are provided only two interchangeable optical systems in FIG. 3, there are preferably provided more interchangeable optical system according to the purpose. In FIG. 5 there are provided diaphragms of four different shapes, but the diaphragm plate 10 may of course be provided with diaphragms of any forms in relation to the interchangeable optical systems 4, 5.

In the foregoing embodiment, the diaphragm plate 10 is provided in the measuring optical system for the laterally scattered light, but a similar effect can be obtained also in the measuring optical system for the forward scattered light by providing said system with said diaphragm plate 10 at a position conjugate with the irradiating beam B in the flow cell 1 with respect to the condenser lens 7. A further improved result can be obtained if such diaphragm plates are provided in both measuring optical system for the forward and laterally scattered lights.

The foregoing embodiment is constructed as a flow cytometer of so-called closed type in which the laser beam irradiates in a flow cell, but the present invention is applicable also to a flow cytometer of so-called jet-in-air type in which the laser beam irradiates outside a flow cell.

Furthermore, in the foregoing embodiment, the diaphragm 10 is rotated by the motor 18 to change the form of diaphragm, but the diaphragm plate 10 may perform a translational movement by the use of a solenoid.

What I claim is:

1. A particle analyzing apparatus, comprising:
    an irradiating optical system for irradiating a particle to be examined flowing one by one with a laser light beam;
    a measuring optical system for measuring at least fluorescent light received from the particle;
    a variable lens system for varying the form of the laser light beam provided in said irradiating optical system; and
    means for varying the form of a viewing field provided at a position in said measuring optical system optically conjugate with the position of the particle to be irradiated by the laser light beam and adapted to vary the form of the viewing field substantially simultaneously with a change in the form of the laser light beam.

2. A particle analyzing apparatus according to claim 1 wherein said variable lens system is provided with plural lenses of respectively different focal lengths.

3. A particle analyzing apparatus according to claim 2 wherein said variable lens system comprises plural sets of beam diameter varying optical systems and cylindrical lens systems of respectively different focal lengths.

4. A particle analyzing apparatus according to claim 1, wherein said variable lens system comprises a zoom lens.

5. A particle analyzing apparatus according to claim 1, wherein said means for varying the form of viewing field is adapted to interchange plural diaphragms of respectively different aperture forms.

6. A particle analyzing apparatus according to claim 5, wherein said means for varying the form of viewing field is adapted to rotate a diaphragm plate provided with plural diaphragms of respectively different aperture forms.

7. A particle analyzing apparatus according to claim 6, wherein said diaphragm plate is rotated in response to the detection of a change in the form of the light beam by said means for varying the form of the light beam.

8. A particle analyzing apparatus according to claim 5, wherein said plural diaphragms comprise a rectangular aperture.

9. A particle analyzing apparatus according to claim 1, wherein, in response to the selection of a form by said variable lens system form of light beam, said means for varying the form of viewing field selects a viewing field of a form which is approximately equal to the form of said light beam.

* * * * *

UNITED STATES PATENT AND TRADEMARK OFFICE
CERTIFICATE OF CORRECTION

PATENT NO. : 4,896,961

DATED : January 30, 1990

INVENTOR(S) : Yuji Ito

It is certified that error appears in the above-identified patent and that said Letters Patent is hereby corrected as shown below:

COLUMN 4:

Line 58, "form" should read --form of the light beam--.

Line 59, "system form of light beam," should read --system,--.

Signed and Sealed this

Fourth Day of August, 1992

Attest:

DOUGLAS B. COMER

*Attesting Officer*     Acting Commissioner of Patents and Trademarks